United States Patent
Stalder et al.

(10) Patent No.: US 12,193,501 B2
(45) Date of Patent: Jan. 14, 2025

(54) HEATING SYSTEM AND METHOD FOR AN INHALER DEVICE

(71) Applicant: JT International S.A., Geneva (CH)

(72) Inventors: Roland Stalder, Zürich (CH); Daniel Wilhelm, Zürich (CH); Andrew Robert John Rogan, Forres (GB)

(73) Assignee: JT International S.A. (CH)

( * ) Notice: Subject to any disclaimer, the term of this patent is extended or adjusted under 35 U.S.C. 154(b) by 138 days.

(21) Appl. No.: 15/780,933

(22) PCT Filed: Dec. 2, 2016

(86) PCT No.: PCT/EP2016/079670
§ 371 (c)(1),
(2) Date: Jun. 1, 2018

(87) PCT Pub. No.: WO2017/093535
PCT Pub. Date: Jun. 8, 2017

(65) Prior Publication Data
US 2018/0343922 A1    Dec. 6, 2018

(30) Foreign Application Priority Data
Dec. 3, 2015  (EP) .................................... 15197837

(51) Int. Cl.
*A24F 40/485*    (2020.01)
*A24F 40/10*     (2020.01)
(Continued)

(52) U.S. Cl.
CPC ............ *A24F 40/46* (2020.01); *A24F 40/485* (2020.01); *A24F 40/10* (2020.01); *A61M 11/042* (2014.02)

(58) Field of Classification Search
CPC .......... A24F 40/10; A24F 40/40; A24F 40/42; A24F 40/46; A24F 40/48; A24F 40/485;
(Continued)

(56) References Cited

U.S. PATENT DOCUMENTS 5,666,977 A * 9/1997 Higgins .................. A24F 40/48
131/194
6,155,268 A    12/2000 Takeuchi
(Continued)

FOREIGN PATENT DOCUMENTS

CN   104287098 A   1/2015
CN   104323432 A   2/2015
(Continued)

OTHER PUBLICATIONS

Extended European Search Report for EP Application No. 15197837.6, dated Feb. 10, 2016.
(Continued)

*Primary Examiner* — Philip Y Louie
*Assistant Examiner* — Sonny V Nguyen
(74) *Attorney, Agent, or Firm* — Lerner David LLP

(57) ABSTRACT

A heating system is provided for an inhaler device, such as an e-cigarette or a personal vaporizer device, for generating an aerosol or a vapour from a liquid to be heated. The system comprises: at least one supply channel for conveying a liquid to be heated from a supply reservoir under capillary action or surface tension forces within the at least one channel; and heating means arranged at an outlet of the at least one supply channel and configured to heat the substance as it emerges from the outlet of the at least one channel. The heating means preferably comprises at least one heating element which extends across a width or an outlet opening of the supply channel and is typically confined to the outlet of the supply channel.

13 Claims, 3 Drawing Sheets

(51) Int. Cl.
*A24F 40/46* (2020.01)
*A61M 11/04* (2006.01)

(58) Field of Classification Search
CPC ...... A24F 47/00; A24F 47/002; A24F 47/004; A24F 47/008
See application file for complete search history.

(56) References Cited

U.S. PATENT DOCUMENTS

| | | | |
|---|---|---|---|
| 2003/0108342 A1 | 6/2003 | Sherwood et al. | |
| 2008/0092912 A1 | 4/2008 | Robinson et al. | |
| 2011/0309157 A1* | 12/2011 | Yang | A01M 1/2077 239/6 |
| 2014/0060554 A1* | 3/2014 | Collett | H05B 3/265 131/328 |
| 2014/0069424 A1 | 3/2014 | Poston et al. | |
| 2014/0109905 A1* | 4/2014 | Yamada | A61M 15/06 128/203.27 |
| 2014/0190496 A1 | 7/2014 | Wensley et al. | |
| 2014/0286630 A1* | 9/2014 | Buchberger | A61M 11/041 392/395 |
| 2015/0216234 A1* | 8/2015 | Chung | A24F 40/485 131/329 |
| 2015/0216237 A1* | 8/2015 | Wensley | A24F 40/46 131/273 |
| 2016/0262454 A1* | 9/2016 | Sears | A24F 47/008 |
| 2017/0367402 A1* | 12/2017 | Lau | A61M 15/06 |
| 2018/0132532 A1* | 5/2018 | Batista | A24F 40/44 |
| 2018/0220707 A1* | 8/2018 | Biel | A24F 40/40 |
| 2020/0275695 A1* | 9/2020 | Force | A61M 15/06 |
| 2024/0148070 A1* | 5/2024 | Özsun | A24F 40/40 |

FOREIGN PATENT DOCUMENTS

| | | |
|---|---|---|
| CN | 104661338 A | 5/2015 |
| CN | 204483035 U | 7/2015 |
| DE | 102014106589 A1 | 11/2015 |
| EP | 0893071 A1 | 1/1999 |
| EP | 2764783 A1 | 8/2014 |
| EP | 3127441 A1 | 2/2017 |
| JP | 2005511178 A | 4/2005 |
| JP | 2018509158 A | 4/2018 |
| KR | 200470732 Y1 | 1/2014 |
| WO | 2011042212 A1 | 4/2011 |
| WO | 2014138244 A1 | 9/2014 |
| WO | 2015/086316 A1 | 6/2015 |
| WO | 2015114325 A1 | 8/2015 |
| WO | 2016079152 A1 | 5/2016 |
| WO | 2016145072 A1 | 9/2016 |

OTHER PUBLICATIONS

International Search Report for EP Application No. 2016079670, dated Mar. 24, 2017.
Communication pursuant to Article 94 (3) EPC, including Written Opinion for Application No. 19186435.4, dated May 31, 2023, pp. 1-4.

* cited by examiner

HEATING SYSTEM AND METHOD FOR AN INHALER DEVICE

CROSS-REFERENCE TO RELATED APPLICATIONS

The present application is a national phase entry under 35 U.S.C. § 371 of International Application No. PCT/EP2016/079670, filed Dec. 2, 2016, published in English, which claims priority to European Application No. 15197837.6 filed Dec. 3, 2015, the disclosures of which are incorporated herein by reference.

FIELD OF THE INVENTION

The present invention relates to an inhaler device, such as an electronic cigarette (e-cigarette), a personal vaporizer or an electronic vapour delivery system. More particularly, the invention relates to a heating system for such an inhaler device and a method of heating for generating an aerosol or a vapour from a substance to be heated in such a device.

BACKGROUND OF THE INVENTION

Inhaler devices of the above types, namely e-cigarettes and personal vaporizers and electronic vapour delivery systems, are proposed as an alternative to traditional smoking articles, such as cigarettes, cigarillos, cigars and the like. Typically, these inhaler devices are designed to heat a liquid solution or a gel to produce or generate an aerosol and/or a vapour to be inhaled by a user. This liquid or gel is usually a solution of propylene glycol (PG) and/or vegetable glycerin (VG), and typically contains a flavorant or one or more concentrated flavours.

Despite the increasing demand for these inhaler devices and the growing market, efforts are still required to develop the performance of these devices, with a view to offering more efficient and improved products. For example, these efforts are directed to an improved aerosol and/or vapour generation, improved aerosol and/or vapour delivery, and more efficient use of energy in aerosol and/or vapour generation to improve the energy consumption, e.g. to enhance the battery life of the device.

SUMMARY OF THE INVENTION

In view of the above, an object of the invention is to provide a new and improved inhaler device, especially an electronic cigarette, and more particularly a new and improved heating system and method for generating an aerosol and/or a vapour from a substance in such an inhaler device.

In accordance with the invention, a heating system having the features recited in claim 1 and a method as recited in claim 10 are provided. Various advantageous and/or preferred features of the invention are recited in the dependent claims.

According to one aspect, therefore, the present invention provides a heating system for an inhaler device, such as an e-cigarette or a personal vaporizer, for generating an aerosol and/or a vapour from a substance to be heated. The system comprises: at least one supply channel for conveying a substance to be heated from a supply reservoir under capillary action or surface tension forces within the at least one channel; and heating means arranged at an outlet of the at least one supply channel and configured to heat the substance as it emerges from the outlet of the at least one channel.

In a preferred embodiment, the heating means is confined to or limited to an outlet region of the supply channel. The heating means typically comprises at least one heating element and the at least one heating element preferably extends across a width of the supply channel, especially across an outlet opening of the supply channel. In this regard, the heating means may be arranged at least partially, and optionally entirely, outside of the supply channel.

In a preferred embodiment, the at least one heating element includes one or more of an electrically conductive wire, strip, foil, or a conductive coating. The foil or the conductive coating may, for example, be provided as a layer or coating around the outlet opening of the supply channel. The material of the wire, strip, foil or coating will be selected from known electrically conductive materials by a person skilled in the art.

In a preferred embodiment, the heating system comprises a plurality of supply channels for conveying the substance to be heated under capillary action or surface tension forces. The heating means is arranged at an outlet of each supply channel and is configured to heat the substance as it emerges from the outlet of each channel. The heating means typically comprises at least one heating element and the at least one heating element preferably extends across a width of each supply channel, and especially across an outlet opening of each supply channel. In this regard, the heating means may be arranged at least partially, and optionally entirely, outside of each supply channel. The plurality of supply channels may be arranged in at least one array, such as in at least one row, and the at least one heating element may comprise an elongate element which extends across the outlet opening of each supply channel in the array.

In a preferred embodiment, the at least one supply channel is formed in a body member which is configured to extend from the supply reservoir to a chamber in the inhaler device from which the aerosol and/or vapour is inhaled. In this regard, the body member is preferably comprised of glass or a ceramic. The body member preferably includes a groove or recess at the outlet region of each supply channel for accommodating the at least one heating element. The groove or recess preferably extends transverse to a longitudinal extent of the supply channel. In this regard, the at least one heating element preferably seats in, or is accommodated in, the groove or recess at the outlet region of each supply channel. Specifically, the at least one heating element may be fused or bonded with the material of the body member, e.g. glass or ceramic, in which the at least one supply channel is formed, with the at least one heating element preferably extending transverse to or across the longitudinal extent of the supply channel. In this way, vaporization may take place directly at the exit or outlet of each supply channel.

In a preferred embodiment, each supply channel is formed as a capillary tube or as a capillary slot. In the case of a capillary tube, the body member may therefore comprise a tubular member defining a capillary channel there-through. In the case of a capillary slot, the body member may comprise at least one, and preferably a pair of plate elements, which define(s) the slot-like supply channel. In this regard, the body member preferably includes a pair of plate elements which are arranged substantially parallel and facing one another in spaced apart relation to define a slot-like supply channel there-between.

In a preferred embodiment, the at least one supply channel has a length in the range of 2 to 20 mm, and more preferably in the range of 5 to 10 mm.

In a preferred embodiment, the at least one supply channel has an inner diameter in the range of 0.1 to 3.0 mm, and more preferably in the range of 0.5 to 1.0 mm.

In a preferred embodiment, the heating system is combined with or incorporated in a cartridge or reservoir assembly for the inhaler device or e-cigarette. In this way, the body member in which the at least one supply channel is formed for conveying the liquid to be heated from the reservoir may be attached to or incorporated in a housing of the cartridge or reservoir assembly which forms the reservoir for storing or holding the liquid.

In a preferred embodiment, the heating system includes a liquid sensor, such as a capacitance sensor, provided along in the at least one supply channel to detect or sense the presence of the liquid. For example, the sensor may be provided at or directly upstream of the outlet of the supply channel. In this way, when the sensor detects or senses the liquid, the system may be controlled to activate the heating element. This may therefore assist optimization of energy consumption, enabling the heating element to be activated only when the liquid is present at the outlet for vaporization. The system may also be configured to generate a signal if the sensor does not detect liquid reaching the outlet for vaporization within a predetermined time. This may indicate a low liquid level in the reservoir.

According to another aspect, the invention provides an inhaler device, such as an electronic cigarette or personal vaporizer, for producing an aerosol and/or vapour from a substance to be heated, especially a liquid or a gel, wherein the inhaler device includes a heating system according to any of the embodiments described above.

In a preferred embodiment, one or more air inlets of the inhaler device are located proximate to an outlet of each supply channel (e.g. each capillary tube or capillary slot) in a chamber in the inhaler device from which the aerosol and/or vapour is inhaled. In this way, airflow into a vapour chamber of the inhaler device is close to or directly adjacent to the heating system at which the vapour is generated for inhalation by a user. The one or more air inlets of the inhaler device are preferably configured and/or arranged as to direct the airflow across the outlets of the supply channels.

According to a further aspect, the present invention provides a method of heating a substance, especially a liquid or gel, in an inhaler device, such as an e-cigarette or a personal vaporizer, the method comprising:

conveying the substance to be heated from a supply reservoir through at least one supply channel by capillary action or surface tension forces; and heating the substance at an outlet of the at least one supply channel as the substance emerges from the outlet of the supply channel.

In a preferred embodiment, the step of heating the substance is performed by one or more electrical heating element which extends across a width of the supply channel, especially across an outlet opening of the supply channel. In this regard, the heating means may be arranged at least partially, and optionally entirely, outside of the supply channel. The electrical heating element is typically confined or limited to the outlet region of the supply channel and/or is provided outside of the supply channel. In a preferred embodiment, the step of heating the substance is carried out on a periodical or intermittent basis, for example, desirably in a pulsed or alternating manner.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which.

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will further be appreciated that certain actions and/or steps in an embodiment of a method may be described or depicted in a particular order of occurrences while those skilled in the art will understand that such specificity with respect to sequence is not actually required. It will also be understood that the terms and expressions used in the present specification have the ordinary meaning as is accorded to such terms and expressions with respect to their corresponding respective areas of inquiry and study, except where specific meanings have otherwise been set forth herein.

DETAILED DESCRIPTION OF EMBODIMENTS

Figure 1:
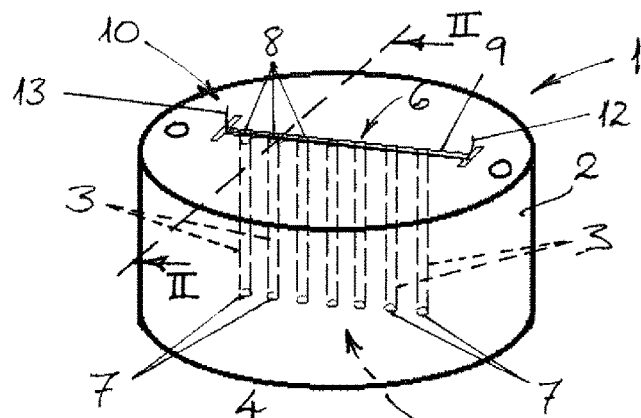
FIG. 1 is a schematic perspective view of a heating system according to an embodiment of the invention.
Figure 2:
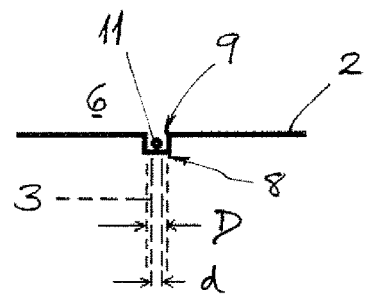
FIG. 2 is a cross-sectional view of the part of the heating system shown in FIG. 1 taken in the direction of arrows II-II.

With reference to FIG. 1 and FIG. 2 of the drawings, one embodiment of a heating system 1 for generating a vapour from a liquid to be heated in an inhaler device, and especially an e-cigarette (not shown), is illustrated schematically. The liquid may include a solution of propylene glycol, vegetable glycerin, and/or one or more flavours. The heating system 1 comprises a body member 2 in which a plurality of supply channels 3 are provided or formed for conveying the liquid to be heated from a supply reservoir 4 adjacent the body member 2 under capillary action or surface tension forces within the channels 3. In this case, each of the supply channels 3 comprises a capillary tube and the plurality of supply channels 3 are arranged in a straight line or row to convey the liquid to be heated from an inlet side or region 5 of the body member 2 to an outlet side or region 6. In this regard, each supply channel or capillary tube 3 has an internal diameter d of about 0.5 to 0.8 mm, and extends between an inlet opening 7 at the inlet side 5 and an outlet opening 8 at the outlet side 6.

Formed in the outlet side 6 of the body member 2, an elongate groove or recess 9 extends across and communicates with, or interconnects, the outlet openings 8 of each of the supply channels 3. In order to vaporize the liquid conveyed from the reservoir 4 by the capillary tubes 3, heating means 10 is provided comprising one or more elongate heating element 11, such as a wire or filament, located or set in the groove 9. In this regard, for example, the heating element 11 may comprise a wire (e.g. a Nichrome or Kanthal™ wire) having a diameter in the range of 0.05 mm to 0.3 mm (e.g. about 0.1 mm) and a resistance in the range of 1 to 5 ohm for a current in the range of about 1 to 1.5 ampere. The groove 9 has a width D which may be slightly larger than a diameter d of the outlet openings 8 of the capillary tubes 3. Opposite ends 12, 13 of the heating wire 11 are configured and arranged for connection to a power supply in the e-cigarette (not shown) for electrical resistance heating. Thus, the heating means 10 is arranged in and confined to the outlet region 6 of each supply channel 3 and is configured to heat and vaporize the liquid as it emerges from the outlet opening 8 of each of the capillary tubes 3.

Figure 3:
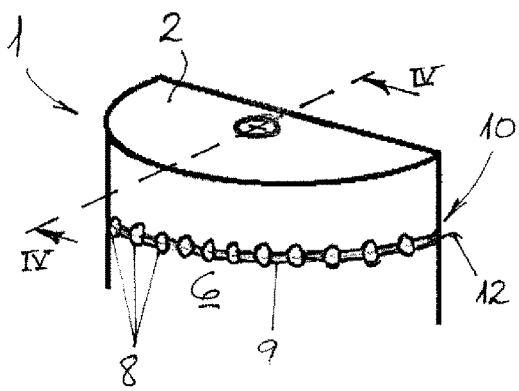
FIG. 3 is a schematic perspective view of part of a heating system according to another embodiment of the invention.
Figure 5:
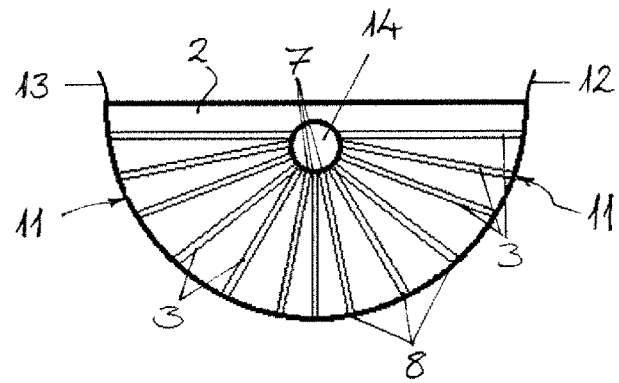
FIG. 5 is a cross-sectional view of the part of the heating system shown in FIG. 4 taken in the direction of arrows V-V.
Figure 4:
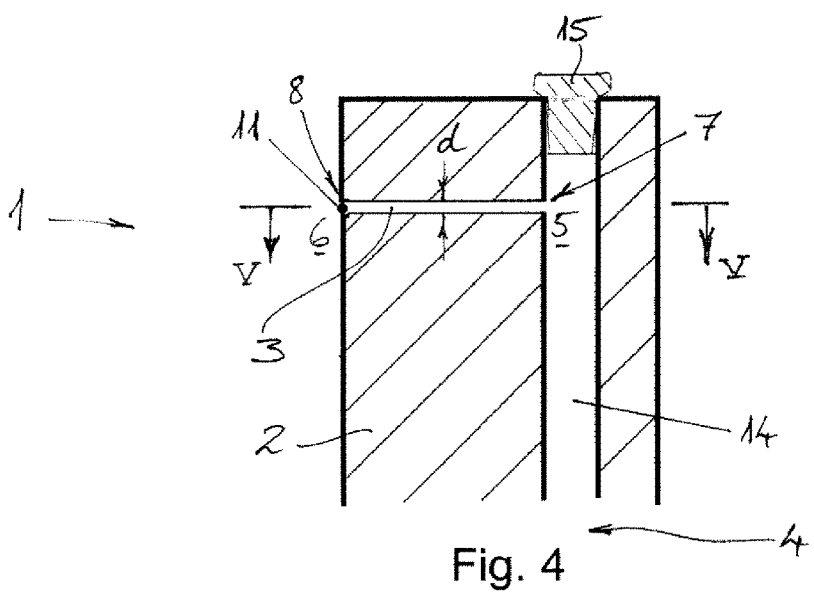
FIG. 4 is a cross-sectional view of the part of the heating system shown in FIG. 3 taken in the direction of arrows IV-IV.

With reference to FIGS. 3 to 5 of the drawings, another embodiment of a heating system 1 for generating a vapour from a liquid to be heated in an e-cigarette (not shown) is illustrated schematically. In this case, the principles of the construction remain essentially unchanged but are applied in an alternative configuration. In particular, the body member 2 comprises an intermediate delivery channel 14 for delivering a liquid to be heated from a reservoir 4 to a plurality of supply channels 3, again formed as capillary with an internal diameter d of about 0.5 to 0.8 mm. Each supply channel or capillary tube 3 extends between an inlet opening 7 at the delivery channel 14 to an outlet opening 8 at an outlet side 6 of the body member. In this embodiment, the supply channels 3 are arranged in a radial array, such that the outlet opening 8 of each capillary tube 3 lies on a semicircular periphery of the body member 2. Again, a groove or recess 9 is formed in the outlet region 6 of the body member 2 and extends across and communicates with, or interconnects, the outlet openings 8 of each of the supply channels 3. Again also, heating means 10 is provided comprising one or more elongate heating element 11, such as a wire or filament, which is located or set in the groove 9. In this way, the heating wire 11 is arranged and configured to heat and vaporize the liquid as it emerges from the outlet opening 8 of each capillary tube 3. A venting cap or stopper 15 may be set or provided in an end of the delivery channel 14. This cap or stopper 15 may be gas-permeable to allow gas exchange with the reservoir 4 to enhance liquid flow through the capillary tubes 3, but may nevertheless still prevent liquid leakage.

Figure 6:
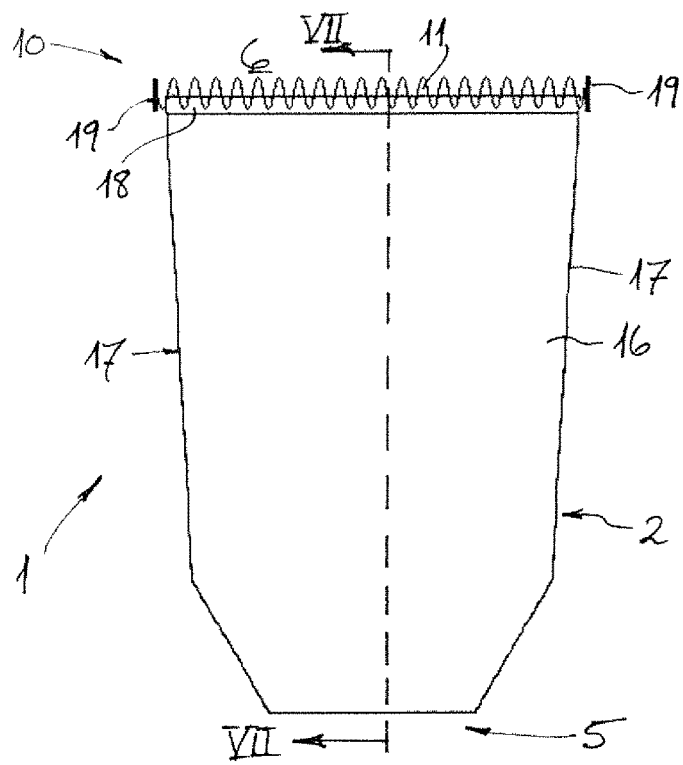
FIG. 6 is a schematic plan view of a heating system according to a further embodiment of the invention.
Figure 7:
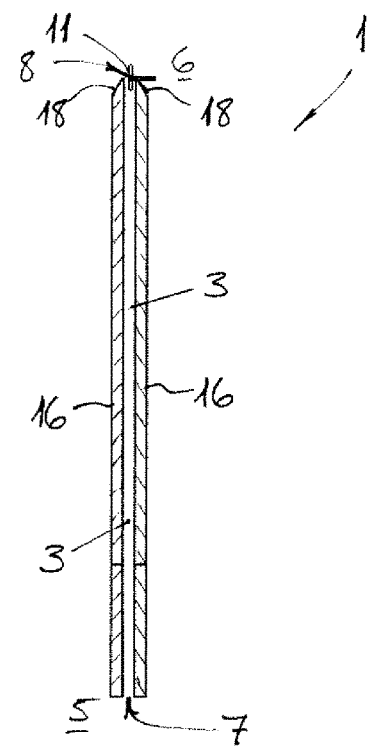
FIG. 7 is a cross-sectional view of the heating system shown in FIG. 6 taken in the direction of arrows VII-VII.

Referring now to FIGS. 6 and 7 of the drawings, a further embodiment of a heating system 1 for generating vapour from liquid to be heated in an e-cigarette is shown schematically. In this embodiment, the plurality of capillary tubes of the previous embodiments are replaced by a supply channel 3 configured as a capillary slot. More particularly, the body member 2 comprises a pair of plate elements 16 which are arranged substantially parallel and facing one another in spaced apart relation to define the slot-like supply channel 3 there-between. The plate elements 16 of the body member 2 extend from an inlet region or inlet end 5 to an outlet region or outlet end 6, with the sides 17 of the plate elements 16 being closed or sealed. The edge 18 of each plate element 16 at the outlet region or outlet end 6 of the slot-like supply channel 3 are chamfered or tapered towards the outlet opening 8 to reduce a surface area presented by the plate elements 16 at the outlet end 6. This acts to reduce the tendency of facing end surfaces of the plate elements 16 at the outlet region 6 to collect or accumulate an excessive volume of the liquid to be heated.

Again, the heating system 1 in FIGS. 6 and 7 includes heating means 10 arranged at the outlet region 6 of the liquid supply channel 3. In this regard, a serpentine heating element 11, such as an electrical resistance heating wire, extends across the outlet opening 8 transversely of the capillary slot 3. As in the two embodiments described above, opposite ends 12, 13 of the heating element 11 are configured and arranged for connection to a power supply in the e-cigarette (not shown) for electrical resistance heating. For this reason, electrical connectors 19 are provided at each of the opposite ends 12, 13 of the heating element 11. Thus, the heating means 10 is again arranged in and confined to the outlet region 6 of the supply channel 3 for vaporizing the liquid as it emerges from the outlet opening 8 of the supply channel 3.

Figure 8A:
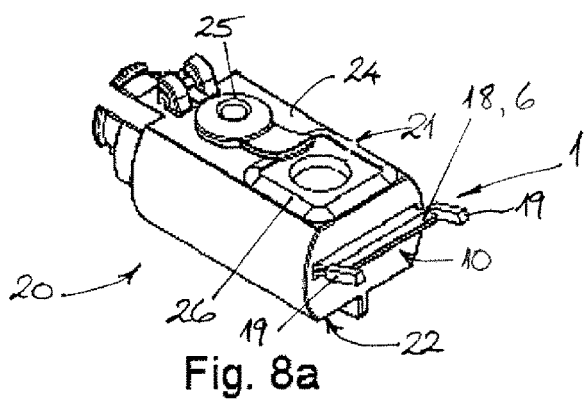
FIG. 8*a* is a schematic perspective view of a cartridge or reservoir assembly of an electronic cigarette device having a heating system according to the embodiment of FIGS. 6 and 7.
Figure 8C:
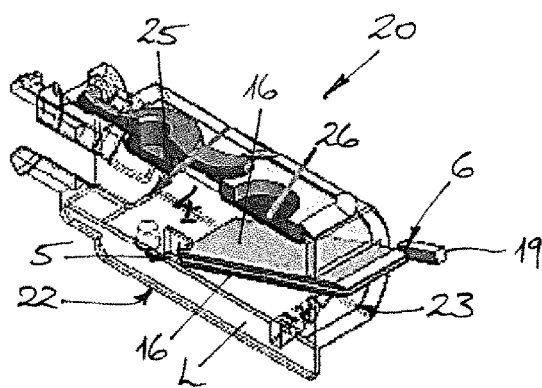
FIG. 8*c* is a schematic partially sectioned perspective view of the cartridge or reservoir assembly shown in FIG. 8*a;*
Figure 8B:
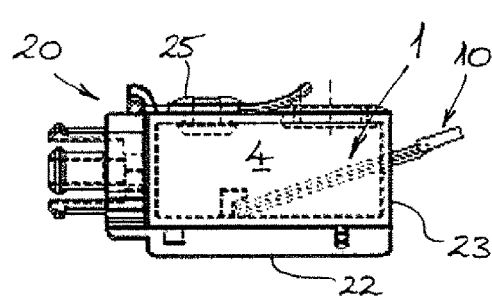
FIG. 8*b* is a schematic side view of the cartridge or reservoir assembly shown in FIG. 8*a;*
Figure 9:
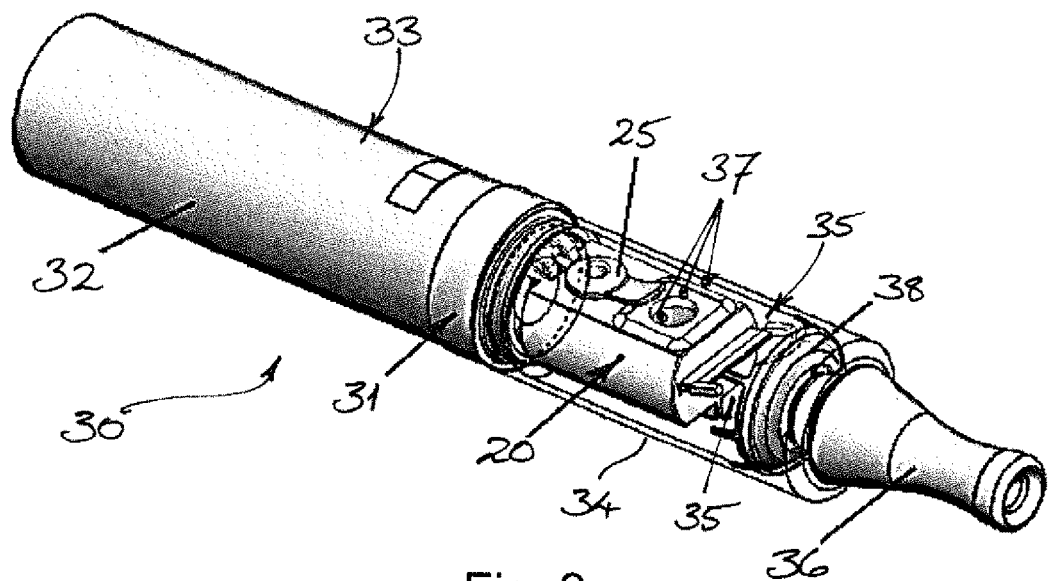
FIG. 9 is a schematic perspective view of an inhaler device, especially an electronic cigarette, according to an embodiment of the invention and including a cartridge or reservoir assembly as shown in FIG. 8*a;*

With reference now to FIGS. 8a-8c and 9 of the drawings, an example is provided of how the heating system 1 shown in FIGS. 6 and 7 may be included in a cartridge or reservoir assembly 20 of an electronic cigarette 30. As can be seen in FIG. 9, the electronic cigarette 30 has a generally cylindrical casing 31, a first portion 32 of which houses or encloses a power supply 33 in the form of a battery unit. The first portion 32 of the casing 31 is coupled to a second casing portion 34, which houses or encloses the cartridge or reservoir assembly 20. As can be seen in FIGS. 8a-8c, the cartridge 20 comprises a housing 21 which encloses a barrel-like reservoir or tank 4 for holding or storing a volume of the liquid L to be vaporized and inhaled during use of the e-cigarette 30. The heating system 1 of FIGS. 6 and 7 is included in the cartridge 20 such that the plate elements 16 extend into the reservoir 4 with the inlet region or inlet end 5 fixed at a base wall 22 of the housing 21 submerged below and/or covered by the liquid L. The plate elements 16 extend upwards at an oblique angle out of an end wall 23 of the housing 21, such that the outlet region or outlet end 6 and the heating means 10 are located within a vapour chamber 35 of the second casing portion 34. An upper side or wall 24 of cartridge housing 21 includes a refill opening which is closed and sealed by a resilient plug member 25. Furthermore, the upper side or wall 24 of the housing 21 includes a venting cap or valve 26 which may include a gas-permeable membrane to allow gas exchange with the reservoir 4 to enhance liquid flow through the capillary slot 3, but which nevertheless prevents liquid leakage there-through.

As seen in FIG. 9, a mouthpiece 36 is provided at, or connected to, an end of the second portion 34 of the casing 31 for a user to draw upon the e-cigarette 30 and to inhale the vapour generated by the heating system 1 in the cartridge 20. In this regard, a row of air inlet holes 37 is provided in the second casing portion 34 for inlet or inflow of air into the vapour chamber 35 when a user draws on the mouthpiece 36. The liquid L is vaporized by the heating means 10 at the outlet 6 of the supply channel 3 in the vapour chamber 35 and the vapour is entrained in the airflow stream and carried to the user via a vapour guide 38 and the mouthpiece 36.

Figures 10, 11:
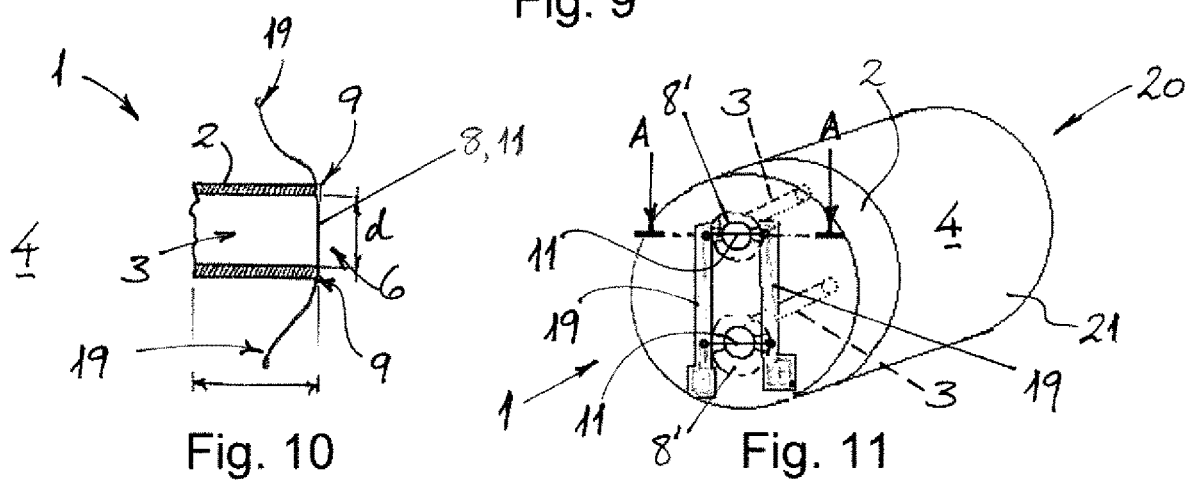
FIG. 10 is a cross-sectional view of a heating system according to a simple embodiment of the invention.
FIG. 11 is a schematic perspective view of a heating system according to an embodiment of the invention incorporated in a reservoir assembly of an inhaler device.

With reference now to FIG. 10 of the drawings, a simple embodiment of a heating system 1 for generating a vapour from a liquid to be heated in an inhaler device, such as an e-cigarette, is shown schematically. The heating system 1 comprises a body member 2 in the form of a tube (e.g. a glass tube) which defines a capillary channel 3 for conveying the liquid to be heated from a supply reservoir 4 adjacent the body member 2 under capillary action. In this case, the capillary channel 3 has an internal diameter d of about 1.0 mm, and extends from the supply reservoir 4 to an outlet opening 8 at the outlet side 6. A groove or recess 9 is formed in the end of the tube 2 at the outlet opening 8 and an elongate heating element 11, such as a wire or filament, is located or set and fused in the groove 9 in connection with the tubular body member 2 with the heating wire 11 extending transversely across the middle of the outlet opening 8.

Referring now to drawing FIG. 11, another embodiment of a cartridge or a reservoir assembly 20 is illustrated schematically. In this embodiment, the heating system 1 comprises a disc-shaped body member 2 which defines two separate and distinct capillary channels 3 for conveying the liquid to be heated from a supply reservoir 4 adjacent the body member 2 under capillary action. In this embodiment, each of the capillary supply channels 3 for conveying the liquid from the reservoir 4 has its own heating element 11, such as a wire or filament. The cross-section of each of the tubes 3 taken in the direction of arrows A may essentially correspond to the example shown in FIG. 10. Each of the heating elements 11 is interconnected by an electrical connector or supply lead 19 for common control and power supply. Each of the heating elements 11 may have a round cross-section or alternatively a flat cross-section for presenting a larger surface area to the liquid emerging from the outlet opening 8 of each channel 3. Furthermore, the outlet opening 8 of each channel 3 may be formed with a diverging conical surface 8' forming a small well for accumulating the liquid and presenting a larger surface area to each respective heating element 11.

Figure 12:
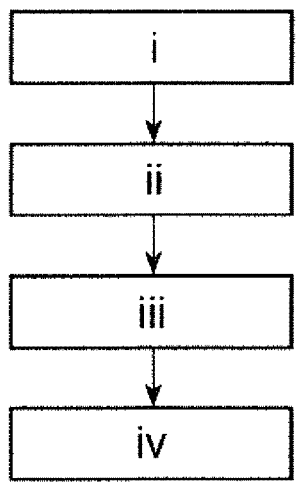
FIG. 12 is a flow diagram which schematically represents a method according to an embodiment of the invention.

Finally, referring to FIG. 12 of the drawings, a flow diagram is shown that illustrates schematically the steps in a method of heating a substance, especially a liquid L in an inhaler device 30, such as an e-cigarette, according to any of the embodiments of the invention described above with respect to FIGS. 1 to 11. In this regard, the first box i of FIG. 12 represents the step of conveying the liquid to be heated from a supply reservoir 4 through at least one supply channel 3, and optionally multiple supply channels 3, by capillary action or surface tension forces. The second box ii then represents the step of heating the liquid L exclusively at an outlet 6 of each supply channel 3 as the liquid emerges from the outlet 6 of the supply channel 3 to vaporize the liquid. The third box iii represents the step of controlling activation of the heating step to depend upon use of the inhaler device 30 by a user. The final box iv in FIG. 12 of the drawings represents the optional step of carrying out the heating of the liquid on a periodical or intermittent basis, especially in a pulsed manner.

Although specific embodiments of the invention are illustrated and described herein, it will be appreciated by those of ordinary skill in the art that a variety of alternate and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

LIST OF DRAWING SIGNS 1 heating system
2 body member
3 supply channel or capillary tube or capillary slot
4 reservoir
5 inlet side or inlet region
6 outlet side or outlet region
7 inlet opening
8 outlet opening
8' conical surface
9 groove or recess
10 heating means
11 heating element or heating wire
12 end of heating element
13 end of heating element
14 delivery channel
15 venting cap or stopper
16 plate element
17 side of plate element
18 chamfered or tapered edge of plate element
19 electrical connector
20 cartridge or reservoir assembly
21 cartridge housing
22 base wall of housing
23 end wall of housing 24 upper side or wall of housing
25 plug member
26 venting cap or valve
30 electronic cigarette
31 casing
32 first casing portion
33 power supply or battery unit
34 second casing portion
35 vapour chamber
36 mouthpiece
37 air inlet
38 clamping ring or vapour guide
D width of groove or recess
d diameter of outlet opening
L liquid to be heated

The invention claimed is:

1. A heating system for an inhaler device configured to generate an aerosol or a vapour from a liquid to be heated, the system comprising:
    an intermediate delivery channel for conveying a liquid to be heated from a supply reservoir;
    a plurality of supply channels in fluid communication with the intermediate delivery channel for conveying the liquid under capillary action or surface tension forces, each of the plurality of supply channels extending from the intermediate delivery channel to an outlet of a respective supply channel; and
    a heating arrangement arranged at the outlet of the plurality of supply channels;
    wherein the heating arrangement comprises at least one electrical heating element including at least one wire,
    wherein the intermediate delivery channel and the plurality of supply channels are formed in a body member which is configured to extend from the supply reservoir to a vapour chamber in the inhaler device from which the aerosol or vapour is inhaled,
    wherein the body member includes a groove or recess formed on an outer surface of the body member at the outlets of each one of the plurality of supply channels, and
    wherein the at least one wire is disposed in the groove or recess outside of the plurality of supply channels and is confined to the outlet of the supply channels such that the at least one wire extends across the outlet of each of the plurality of supply channels to heat the liquid at the outlet of the supply channels.

2. The heating system according to claim 1, wherein the groove or recess is curved and extends about at least a portion of the body member.

3. The heating system according to claim 1, wherein each one of the plurality of supply channels is formed as a capillary tube and/or a capillary slot, and wherein the body member in which each supply channel is formed is comprised of glass or a ceramic.

4. The heating system according to claim 1, wherein at least one of the plurality of supply channels has a length in a range of 2 to 20 mm.

5. The heating system according to claim 4, wherein the at least one of the plurality of supply channels has a length in the range of 5 to 10 mm.

6. The heating system according to claim 1, wherein at least one of the plurality of supply channels has a diameter in a range of 0.1 to 3.0 mm.

7. The heating system according to claim 6, wherein the at least one of the plurality of supply channels has a diameter in the range of 0.7 to 2.0 mm.

8. The heating system according to claim 1, wherein the at least one electrical heating element further includes a coating provided around the outlet of the plurality of supply channels.

9. An inhaler device, for producing an aerosol and/or vapour from a liquid or a gel to be heated, wherein the inhaler device includes the heating system according to claim 1.

10. The inhaler of claim 9, wherein the inhaler device is an electronic cigarette or a personal vaporizer.

11. A method of heating a substance in an inhaler device, the method comprising:
    conveying the substance to be heated from a supply reservoir through an intermediate delivery channel and then through a plurality of supply channels by capillary action or surface tension forces, wherein the intermediate delivery channel and the plurality of supply channels are formed in a body member; and
    heating the substance at an outlet of the supply channels;
    wherein the step of heating the substance is performed by one or more electrical heating elements comprising at least one wire,
    wherein the body member includes a groove or recess formed on an outer surface of the body member at the outlets of each one of the plurality of supply channels, and
    wherein the at least one wire is disposed in the groove or recess outside the supply channels and is confined to the outlet of the supply channels such that the at least one wire extends across the outlet of the supply channels to heat the substance at the outlet of the supply channels.

12. The method according to claim 11, wherein the step of heating the substance is carried out on a periodical or intermittent basis.

13. The method according to claim 12, wherein the step of heating the substance is carried out in a pulsed or alternating manner.

* * * * *